United States Patent [19]

Burton et al.

[11] Patent Number: 5,229,374
[45] Date of Patent: Jul. 20, 1993

[54] METHOD FOR TREATMENT OF LOWER GASTROINTESTINAL TRACT DISORDERS

[76] Inventors: Albert F. Burton, 297 Rodello Street, Comox, B.C., Canada, V9N 4Z9; Hugh J. Freeman, 2211 Wesbrook Mall, Vancouver, B.C., Canada, V6T 2B5

[21] Appl. No.: 826,762

[22] Filed: Jan. 28, 1992

[51] Int. Cl.$^5$ .............................................. A61K 31/70
[52] U.S. Cl. ..................................................... 514/62
[58] Field of Search .......................................... 514/62

[56] References Cited

U.S. PATENT DOCUMENTS 3,697,652 10/1972 Rovati et al. .
4,006,224 2/1977 Prudden .
4,590,067 5/1986 Meisner .

FOREIGN PATENT DOCUMENTS

WO 87/02244 4/1987 PCT Int'l Appl. .

OTHER PUBLICATIONS

Olaison et al., "Abnormal Intestinal Permeability in Crohn's Disease", *Scand. J. Gastroenterol.*, 25: 321–328, 1990.
Hollander et al., "Decreased Intestinal Permeability in Patients with Crohn's Disease and Their Relatives", *Annals of Internal Medicine*, 105: 883–885, 1986.
Burton et al., "Decreased Incorporation of $^{14}$C--Glucosamine Relative to $^3$H-N-Acetyl Glucosamine in the Intestinal Mucosa of Patients with Inflammatory Bowel Disease", *Amer. Journal of Gastroenterology*, vol. 78, No. 1, pp. 19–22, 1983.
Greenspan et al., "Oral Manifestations of Disease", *Harrison's Principles of Internal Medicine*, 12th ed., Ch. 41, 1991, McGraw-Hill.
Schloss, "Extraintestinal Manifestations", *Idiopathic Inflammatory Bowel Disease*, Thomson A. B. R. ed., M.O.M. Printers, Ottawa, 1982, Ch. 23.
Umetsu et al., "Effect of Proglumide on Glycoprotein Synthesis in Aspirin-Induced Gastric Erosions in Rats", *European Journal of Pharmacology*, 69:69–77, 1980.

*Primary Examiner*—Leonard Schenkman
*Attorney, Agent, or Firm*—Barrigar & Oyen

[57] ABSTRACT

This invention relates to the novel use of N-acetyl glucosamine for the treatment of gastrointestinal tract disorders by restoring and maintaining the integrity and normal function of the gastrointestinal tract. A method of treating gastrointestinal mucous membrane disorder in a human being comprising feeding the human being a therapeutic amount of N-acetyl glucosamine on a periodic basis.

6 Claims, No Drawings

METHOD FOR TREATMENT OF LOWER GASTROINTESTINAL TRACT DISORDERS

FIELD OF THE INVENTION

This invention relates to the novel use of N-acetyl glucosamine for the treatment of lower gastrointestinal tract disorders by restoring and maintaining the integrity and normal function of the gastrointestinal tract.

BACKGROUND OF THE INVENTION

Mucous membranes of the entire digestive tract, including the oral cavity, are composed of epithelial cells which have a short life span. This life span varies with the location along the tract but it is estimated that the average cell along the tract has a life of about 2 to 3 days. There is in the tract a constant replenishment by cell division, which has the effect of renewing the lining of the digestive tract constantly so that injuries have only a temporary effect and any damage resulting from contact with possibly injurious substances ingested with food are quickly repaired. This rapid renewal process also, however, renders the tissue more susceptible to certain agents which impair cell division, for example, anti-cancer drugs. (Harrison's Principles of Internal Medicine, 12th ed., Ch. 41, 1991, McGraw-Hill).

Periodontal diseases and diseases of oral mucosa usually involve microorganisms, but a number of factors influence the integrity of the tissue itself. For example, it has been shown that about 10% of persons with Inflammatory Bowel Disease have Aphthous ulcers of the mouth (Harrison's Principles, cited, Idiopathic Inflammatory Bowel Disease, Thomson A. B. R. ed., M. O. M. Printers, Ottawa, 1982, Ch. 23). Inflammatory Bowel Disease has been associated with defects in the protective lining of the gastrointestinal tract (Burton A. F., Anderson, F. H., American Journal of Gastroenterology 1983, 78: 19–22; Olafson et al., Scandinavian Journal of Gastroenterology 1990, 25: 321–328; Hollander et al., Annals of Internal Medicine 1986, 05: 883–885).

The mucosa of the mouth has a high rate of cell turnover as does the rest of the digestive tract and what applies to tissue elsewhere in the tract has equal significance in the oral cavity. Proglumide, a drug which protects against an ulcer in the stomach, has been reported to increase the synthesis of glycoproteins and glycosaminoglycans, which are considered to provide protection by maintaining the integrity of the lining of the stomach (Umetsu T. et al., European Journal of Pharmacology 1980, 69: 69–77).

Several patents disclose amino sugars for treatment of disorders.

U.S. Pat. No. 4,590,067, May 20, 1986, Meisner, Peritain Ltd., discloses a composition for preventing and treating periodontal disease comprising bone meal, ascorbic acid, tyrosine and either glucosamine or cysteine. N-acetyl glucosamine is not disclosed.

French Patent No. 2,473,887, Jul. 24, 1981, discloses the use of biochemical precursors of glucosaminoglycans for the treatment of vascular disorders of functional or organic origin in which there is insufficient blood flow to the limbs, for asphyxic hypoxydotic symptoms, and in cosmetology, for skin defects caused by insufficient circulation to the skin. The precursors, which include N-acetylglucosamine, increase the elasticity of perivascular tissue, resulting in an increase in arterio-capillary blood flow, without having a vasodilating action.

U.S. Pat. No. 4,006,224, Feb. 1, 1977, J. F. Prudden, discloses the treatment of ulcerative colitis or regional enteritis in a mammal by administering D-glucosamine, or one of its salts. Equal or superior results to the conventional treatments of the two conditions are obtained. The dose is 20–300 mg/kg of D-glucosamine, HCl daily. In a clinical trial, a patient with Crohn's Disease that was not affected by ACTH or prednisone was given D-glucosamine, HCl subcutaneously. The symptoms stopped after several weeks of treatment.

WO A 8 702 244, N. Hendry, EP A 0178602, Peritain Ltd. and French Patent A 2016 182, Rotta Research Labratorium SpA, are of interest to this subject.

Hendry discloses a preparation for tissue growth regulation comprising (a) at least one of N-acetyl-D-glucosamine or an oligomer thereof, or a deacylated derivative thereof, or a substituted product of these compounds; (b) at least one of biotin or an analog or derivative biotin, or biologically active residue thereof; and (c) a divalent metal cation together with a pharmaceutically acceptable anion.

Both Meisner and Hendry refer to amino sugars, including glucosamine and N-acetyl glucosamine. Their use is as one of a mixture of several other known nutrients, which have various effects on cell growth.

A key difference in the applicant's proposed use of NAG is this: It is proposed as a source of amino sugar for the synthesis of molecules such as glycoproteins and glycosaminoglycans, which are rich in NAG and the synthesis of which is stimulated by NAG.

NAG is formed from glucosamine and NAG is then directly converted into other amino sugars. NAG is thus a key substance, and in the applicant's work with intestinal tissue, it was found that the formation of NAG itself from glucosamine was the slow part of the process. This necessitates the use of NAG, specifically, and not a deacetylated form, or oligomer.

NAG, moreover, is more stable than glucosamine, is a neutral substance and is readily assimilated by tissues and utilized, whereas most oligomers are not.

The proposed use of NAG is unique and differs from existing art.

An article entitled "Decreased Incorporation of $^{14}$C-Glucosamine Relative to $^{3}$H-N-Acetyl Glucosamine in the Intestinal Mucosa of Patients with Inflammatory Bowel Disease", A. F. Burton and F. H. Anderson, vol. 78, No. 1, 1983, American Journal of Gastroenterology, discloses evidence that the synthesis of glycoproteins in intestinal mucosa of patients afflicted with inflammatory bowel disease is deficient in the diseased tissues of such patients. The article discusses possible reasons for the deficiency. However, no suggestions for alleviating the deficiency are made.

SUMMARY OF THE INVENTION

The invention is directed to a method of treating gastrointestinal mucous membrane disorder in a human being comprising feeding the human being a therapeutic amount of N-acetyl glucosamine on a periodic basis.

The N-acetyl glucosamine can be fed to the human being on a daily basis at a dosage of about 300 mg to about 10,000 mg of N-acetyl glucosamine per day, about 1,000 mg to about 6,000 mg of N-acetyl glucosamine per day or about 500 mg of N-acetyl glucosamine per day.

The N-acetyl glucosamine can be incorporated in a pharmaceutically acceptable carrier. The N-acetyl glucosamine can be fed to the human being only as required to restore the integrity of mucous membrane tissues.

The invention is also directed to a composition useful for treating gastrointestinal mucous membrane disorder in a human being comprising N-acetyl glucosamine and a pharmaceutically acceptable carrier. The N-acetyl glucosamine can be present in the amount of about 1,000 mg to about 6,000 mg, or in the amount of about 500 mg.

DETAILED DESCRIPTION OF THE PREFERRED EMBODIMENT

There are tissue defects in the digestive tract of human beings suffering food intolerance or food allergies. These defects can be corrected to enable the mucosa in the tract to form a necessary barrier to transmission of food allergens and to maintain normal function. The mucosa tissue structure is rich in amino sugars derived from N-acetyl glucosamine and we have discovered that the availability of N-acetyl glucosamine is critical to its synthesis.

We have also discovered that an external source of N-acetyl glucosamine is useful to ensure adequate synthesis of the mucosal barrier. Indeed, we have found that the use of N-acetyl glucosamine alone might be sufficient in itself to treat milder food allergy cases. In more severe cases, the amino sugar, N-acetyl glucosamine might be combined with elemental diets so that the removal of offending substances is accomplished, while at the same time, providing the new amino sugar material necessary to enable the human body to generate coherent mucosa tissue and maintain its defenses.

N-acetyl glucosamine (NAG) is an amino sugar, which is formed in all animal cells and is utilized for the synthesis of many cellular components. The biochemical process by which these components are made is similar in all cells although the end products differ depending upon the type of cell involved. Most of the end products are found outside the cells where they form sheaths which bind cells together, and are major structural components, as in the walls of blood vessels, and fill the spaces between cells, i.e. the interstitium. Amino sugars are found combined with other large molecules (macromolecules) of protein, lipid (fats) or other carbohydrates to form glycoproteins (GP), glycolipids (GL) and glycosaminoglycans (GAG). Glycoproteins have many functions, some circulate in the blood, others are anchored on the surface of cells, as are glycolipids. They can confer unique properties to the cell, for example, on the surface of red blood corpuscles there is a glycolipid which determines the blood groups A, B and O. The sole difference between these groups is the presence of a single amino sugar. Such remarkable specificity indicates that there is a "language" in which amino sugars are the "letters" analogous to the genetic code, by which biological information is recorded and put into action.

Each cell makes its own amino sugars and the process, as in the case of most biochemical synthesis, is regulated by the availability of the first member of the sequence, which in this case is glucosamine. Glucosamine is formed from the pool of sugars derived from glucose, blood sugar, and is acetylated to form N-acetyl glucosamine (NAG). NAG is the immediate precursor for two other amino sugars, N-acetyl galactosamine and N-acetyl neuraminic (sialic) acid. These amino sugars constitute about half the total weight of the GAG found in human tissues (References 1-7).

In the synthesis of these molecules, the availability of the substrate, amino sugars, is critical to proper function. We have discovered that although the formation and utilization of amino sugars takes place in all human cells independently, nevertheless an external source of amino sugar is readily taken up by the cells and is utilized by them for incorporation into the macromolecules. An external source of amino sugar, we have found, can provide for an adequate amount of substrate to satisfy cell demands which otherwise might be greater than the cells can meet.

The interstitium is the space between the cells which contains the fibrous protein collagen ensheathed by glycosaminoglycan (GAG). The GAG absorbs very large quantities of water to form a gel-like material which resists compression thereby giving shape and firmness to the tissue. This material acts as a medium which regulates the passage of nutrients, etc., between the blood and the tissues, and also acts as a barrier, for example, to the spread of infection (Bert and Pearce).

Mucous membranes are covered by a microscopically thin glycoprotein rich in sialic acid called the glycocalyx. In the gastrointestinal tract (GI), this microscopically thin layer is the ultimate barrier between the underlying tissue and the corrosive digestive juices. When the layer is damaged, erosion and ulceration of the underlying tissue occurs. If the blood supply to the upper GI is arrested for about 5 minutes, for example, it has been found that all synthetic processes cease, including formation of the glycocalyx, and an ulcer can be seen forming within an hour. This illustrates the dynamic nature of the biological processes in the human body. There are several hundred grams of amino sugar in the various tissue components of the body but the average life of a given molecule is only 3 days or so. There is thus a constant turnover of all molecules in the body, even in tissues such as bone, and a constant supply of substrates for synthesis is therefore required.

An important and novel feature of the present invention is that increased demands caused by injury such as food allergen injury can be placed upon cells which might strain their resources, and in this situation, an external supply of amino sugars is beneficial. In the gastrointestinal tract (GI), the rate of synthesis of the glycocalyx had been considered to be adequate in persons afflicted with Inflammatory Bowel Disease (IBD). However, in these persons, as in many situations where there is disease or injury, the turnover of cells is increased, perhaps as much as threefold. This creates a demand that is beyond what is considered normal. We have found that the incorporation of NAG into the intestinal mucosal tissue is three times greater in persons afflicted with IBD than in those who are not afflicted.

We have also found that in human placenta near term, the formation of glycosaminoglycan (GAG) is stimulated strongly by the steroid 17 $\alpha$-hydroxyprogesterone (Burton et al.) which appears to function by increasing the synthesis of amino sugars. We have discovered that the same stimulation can be achieved merely by providing the appropriate amino sugars.

Others have shown that in chondrocytes, the cells which form cartilage, the presence of corticosteroids inhibits the formation of GAG. Supplying amino sugars largely overcame this inhibition (Fassbender).

In a recent publication, the question of intestinal permeability in persons with Crohn's Disease, a form of IBD, was reviewed (Olaison et al.). It was found that these persons have greater than normal permeability of the GI tract which leads to the absorption into the bloodstream of substances normally excluded. This includes the substances which cause food sensitivities or food allergies. The condition is attributed to a defect in the mucosal barrier, the glycocalyx, and the intercellular cement composed of GG. Even unaffected relatives of these patients have been found to have increased permeability (Hollander et al.) which supports the concept that some individuals have a genetic or constitutional defect which sets the stage for a spectrum of disorders ranging from mild to serious food intolerance to severe inflammatory lesions.

Various agents inhibit the formation of the mucosal barrier including ethanol, aspirin and other anti-inflammatory agents. Erosion and bleeding of the GI tract is a major side-effect of such drugs. An agent, proglumide, which protects against ulcer formation has been shown to stimulate the incorporation of NAG into mucosal glycocalyx and this is considered the reason for its effectiveness (Umetsu).

Inflammation is a common accompaniment of many forms of injury and is part of the body's defence and repair mechanism. Often, however, the inciting agent is such that the inflammation serves no protective purpose and in fact results in tissue damage causing pain and disability, as in arthritis.

There are, therefore, many situations where an external source of amino sugar can be beneficial. We have discovered that a good choice is N-acetyl glucosamine (NAG) which is a neutral compound, is stable, is very soluble, is tasteless, and is readily absorbed from the digestive tract. It circulates in the blood with a half-life about 4 hours and very little is excreted since it is a "committed metabolite" utilized exclusively for the synthesis of GP, GL, GAG in tissue components. An external supply, we have found, is readily taken up and utilized by the human body and therefore has the potential to be of benefit in many situations where the synthetic processes are less than adequate to meet demands. NAG alone is capable of efficient utilization for these processes when taken by mouth.

EXAMPLE 1

Case History S.B.

S.B., female, 55, underwent surgery for Crohn's Disease in 1977, with removal of about 1 m of her terminal ileum. Subsequently, she experienced considerable pain, discomfort, nausea and diarrhea. Cholestyramine has helped the diarrhea by eliminating excess bile salts; she also requires injections of vitamin B12 because of the loss of terminal ileum. She began taking NAG late in 1977, initially at 1 g or so daily, ranging up to 10 g. Usually, she finds about 3 g per day is sufficient to cause marked improvement in digestion, better tolerance of foods, little diarrhea and much improvement in her discomfort level.

She has taken NAG with the approval of her physician for over eleven years and has maintained a reasonably stable condition. S.B. has had intermittent problems, including surgery for abscess, kidney stone, hysterectomy, residual effects of the Crohn's Disease, and the surgeons have reported finding no evidence for active Crohn's Disease. Numerous laboratory and organ function tests have been performed since she started taking NAG. Except for a tendency to require supplements of potassium, other tests have been normal, including blood, urine, thyroid and kidney function. S.B. has held a very responsible position for the past ten years, which she attributes largely to the benefits of NAG in her diet. She would not be able to handle the situation without daily NAG treatment.

EXAMPLE 2

Case History—A.D.

Diagnosis of Crohn's disease was made on A.D. in April, 1988 and surgery or steroid therapy was proposed by the attending internist. This was refused in order instead to test N-acetyl glucosamine (NAG) as a means of possibly avoiding more drastic procedures. Up to 2 g (1 tsp.) per day of NAG was taken by A.D. and the symptoms appeared to be relieved after a few days. During the next few months, symptoms would recur after about one week if A.D.'s intake of NAG was discontinued. After several months of daily NAG ingestion, the symptoms abated and have been in remission for over a year, with the exception of one episode in January, 1988, when there was a temporary recurrence, but it responded to an increased intake of NAG. The disease remains in remission.

EXAMPLE 3

Case History—A.B.

A.B., male, 62, was taking aspirin at a rate of 325 mg per day. Gastrointestinal bleeding began suddenly after a time of taking such aspirin. Black stools (which indicate blood from internal bleeding) were accompanied by considerable fresh blood with every movement. Discomfort in the upper abdomen was felt.

A.B. began taking NAG at a dosage of 3-4 g per day, as soon as intestinal bleeding was observed. A.B. also continued to take aspirin. No other medication was taken, such as antacids. Bleeding began to decrease after 3 days of treatment and was completely gone in 4 days. Thirteen days after bleeding had started, A.B. visited a gastroenterologist who advised terminating the aspirin ingestion. The diagnosis was upper GI, probably duodenal bleeding, likely caused or aggravated by the aspirin. Blood tests indicated that haemoglobin fell from 142 to 109 g per liter, representing a loss of about 25% of blood volume. Subsequently, A.B. began to take NAG and after 4 weeks, the upper abdominal discomfort had disappeared completely. Aspirin consumption was resumed (without the physician's knowledge) but taken together with NAG, A.B. continues to be free of any GI symptoms after 4 months.

EXAMPLE 4

Case History—L.G.

L.G., female, 40, underwent surgery for Crohn's Disease in 1978. She experienced further difficulties and was hospitalized in 1988 where she was fed intravenously. She continued intravenous feeding for some weeks at home after release from the hospital. She still experienced diarrhea and intestinal bleeding for some months. She began taking NAG, 3 g per day, in the fall of 1988. After a couple of weeks, the diarrhea stopped and she felt less discomfort and nausea, and experienced a better tolerance of food. Symptoms recurred after a couple of weeks when she ran out of NAG, but the symptoms disappeared again after a week or so when daily NAG ingestion dosage was resumed. A supply of NAG was not readily available and this pattern occurred on three subsequent occasions. After several weeks of steady treatment with NAG at a rate of 3 g per day, she found that the gastrointestinal (GI) bleeding stopped. She has since found a steady reliable supply of NAG and has continued to take NAG at a daily rate of 3 g for over two years. There has been no recurrence of GI bleeding.

EXAMPLE 5

Case History—R.R.

R.R., male, 42, underwent surgery for Inflammatory Bowel Disease with partial removal of the colon. After the surgery, he continued to suffer rectal bleeding and ulceration of the mouth. He took aspirin and acetaminophen regularly for pain relief, and underwent surgery for hip replacement. He began taking NAG, 3 g per day, before the hip surgery and continued taking it at that rate during and after the surgery. He reported that the main immediate improvement he experienced was less fatigue and nausea, and a generally better feeling However, he also noted after several weeks of NAG ingestion that there was a lessening of rectal bleeding, and a decrease in the development of mouth ulcers.

R.R. then underwent surgery for complete removal of the colon. At the time, he stopped taking NAG. He again began to experience difficulties with intestinal discomfort and mouth ulcers. Subsequent to surgery for removal of the colon, he resumed taking NAG at a rate of 3 g per day and found that as before, it made him feel better and lessened the incidence of mouth ulcers.

In the period before colectomy, the evidence of decreased bleeding is of significance and is consistent with the discovery that NAG provides for the formation of essential tissue structures whose deficiency contributes to GI bleeding and oral cavity lesions.

EXAMPLE 6

Case History—J.F.

Over a period of two or more years, J.F. developed a bowel disorder that caused periods of considerable pain and discomfort. She also developed a persistent psoriasis condition, which did not succumb to treatment with standard psoriasis treatment creams. In September of 1987, J.F. underwent an operation for an unrelated problem and at that time the attendant physician noticed that J.F. had an inflamed bowel. That physician and others that J.F. consulted thereafter offered no particular treatment apart from a possible operation in the event that the condition, which they diagnosed as diverticulitis, became severe.

In late September, 1987, J.F. began taking a daily dose of N-acetyl glucosamine in an amount approximating one teaspoonful (2 g) per day. J.F. dissolved this in fruit juice and sipped the juice at frequent intervals over the daytime. J.F.'s intestinal condition improved a great deal and she had no further serious attacks of diverticulitis. During this time, J.F. underwent a series of X-rays and sigmoidoscope examinations which confirmed that J.F. did indeed have diverticulitis.

By the early part of December, 1987, J.F. was feeling so much better that she decided to reduce the amount of NAG she was consuming daily. J.F. did this gradually until she was down to about ¼ tsp. (0.5 g) per day. In late December, 1987, J.F. had a mild recurrence of the intestinal symptoms that she had experienced previously. J.F. returned to a larger daily dose of NAG, about ¾ tsp. (1.5 g) per day, and the symptoms disappeared. In late January, 1988, J.F. and her husband went on holidays for two weeks during which time her consumption of NAG became somewhat irregular. Shortly before returning home, J.F. had another recurrence of the bowel disorder—again a mild one, but the symptoms subsided about 48 hours after resuming a steady daily intake of NAG. Since then J.F. has maintained a daily dose of NAG amounting to about ¾ tsp. which she takes in three portions, morning, noon and at night before bed. She has been completely symptom-free since then. Her psoriasis condition has also cleared up and is in remission.

When J.F. reduces her daily NAG dosage to less than ¼ tsp. (about 1.0 g) per day, she finds that adverse intestinal and other symptoms recur, including her psoriasis condition. However, consistent treatment with NAG minimizes or eliminates the symptoms.

EXAMPLE 7

Case History—G.O.S.O.

G.O.S.O., male, 55, for about three years, had been suffering from periodic inflammation and mucousal drainage of the lower bowel area, a condition sometimes known as irritable bowel syndrome. For about the same time, G.O.S.O. experienced a problem with psoriasis on each side of his nose. G.O.S.O. consulted his physician to investigate the bowel complaint. The physician conducted an examination and concluded that G.O.S.O. should undergo a barium enema/X-ray examination.

G.O.S.O. attended the radiologist's office after undergoing the prescribed two day liquid diet and the barium enema X-ray testing procedure was conducted. The results of the examination indicated that G.O.S.O. had an inflamed bowel condition known medically as diverticulitis/diverticulosis, which is a condition common for persons who are fifty or more years of age. The physician said that the initial treatment that is usually prescribed for a person afflicted with diverticulitis is a daily supplement of 4 tablespoons of wheat bran. If the supplement of wheat bran did not bring about an improvement, then antibiotics would be prescribed.

G.O.S.O. began to include four tablespoons of wheat bran in his morning breakfast cereal, but over the next two weeks, did not notice any significant improvement in his diverticulitis condition.

G.O.S.O. then commenced to take four 500 mg capsules of N-acetyl glucosamine per day. Within three days of commencing the treatment, G.O.S.O. noticed a very obvious significant reduction in the mucous emission rate from his lower bowel area. G.O.S.O. also noticed that the irritation around his rectum cleared up in a matter of days.

G.O.S.O. continued a daily dosage rate of 2 g of N-acetyl glucosamine for fifteen days. However, G.O.S.O. did not have an opportunity to purchase a replacement of 500 mg. N-acetyl glucosamine capsules. Within three days, G.O.S.O. noticed that there was a recurrence of the mucous discharge from his lower bowel area. Prior to that, the mucous discharge had stopped for about twelve days and there was a dramatic improvement in his inflamed bowel condition.

G.O.S.O. then purchased two 60 capsule containers of 500 mg N-acetyl glucosamine capsules and commenced treatment again at a 2 g per day NAG dosage rate. As before, after about three days of treatment, G.O.S.O. noticed a strong reduction in the anal mucous discharge rate. The problem was cleared up in about five days after recommencing treatment with N-acetyl glucosamine. G.O.S.O. continued taking 2 g of N-acetyl glucosamine per day for six weeks. During that period of time, the mucous discharge due to an inflamed bowel condition was completely terminated.

The psoriasis condition on each side of the lower part of his nose that G.O.S.O. had experienced for about three years, was treated with cortisone steroid anti-fungal creams. This treatment had been largely ineffective. After daily ingestion of 2 g of N-acetyl glucosamine for treatment of the diverticulutis, G.O.S.O. noticed that the psoriasis condition cleared up. There has been no return of the psoriasis condition.

EXAMPLE 8

Case History—TG

Male, 68, experienced chronic constipation and intolerance of some foods, which had been attributed to deficient secretion of mucous in the gastrointestinal tract. He began taking NAG, 3 g per day, in 1988 and reported normalization of bowel function without the need for oil or other laxatives. His tolerance of foods improved simultaneously and he also reported that a nasal allergy improved greatly Symptoms recurred in one to two weeks when his supply of NAG ran out but came under control in a week or two upon resuming NAG. He claims he needs at least 3 g of NAG per day for effective control.

EXAMPLE 9

Case History—G.E.D.

G.E.D. is professor emeritus of the Faculty of Medicine, The University of British Columbia, Vancouver, B.C., Canada. For many years, G.E.D. suffered from a variety of food sensitivities. Reactions had sometimes been dramatic, and even at one instance put him in the Emergency Department at Vancouver General Hospital, Vancouver, B.C., Canada. The sensitivities started with orange juice, but subsequently expanded to include meat, milk products, corn, etc. G.E.D. had been able to control them, for the most part, by adhering closely to a rotation of dietary components every four days and refraining from eating in restaurants. Gradually, his symptoms abated but he still had episodes of pain and discomfort that he attributed to dietary causes. In November, 1990, he received a trial supply of N-acetyl glucosamine (NAG), taking it with him on a trip to California, Texas and Florida. Whereas normally he would have expected at least some dietary and food sensitivity problems on such a trip, he experienced none. Since then, he has been much less troubled by symptoms, and these have quickly abated whenever he took a dosage of NAG.

Because of the variability of his response to food, it has taken some months to evaluate the effect of NAG, but G.E.D. is positive it helps considerably. Recently, his daughter, who has similar problems, had persistent pain after drinking orange juice. This intestinal pain responded quickly to ingestion of the NAG that G.E.D. gave her.

EXAMPLE 10

Case History—TL

T.L., male, age 23, began suffering sharp abdominal pain in 1985, and a general intolerance of foods except for rice and a few other things. He could not tolerate fibre, fried foods, etc. He was prescribed an anti-ulcer regime which caused little improvement. In 1987, he was given cimetidine and sulcrate, anti-ulcer agnets. Colonoscopy and gastroduodenoscopy in 1987–88 were negative. He was also diagnosesd as asthmatic, and allergic to grass, dust, trees, hair and some foods.

T.L. began ingesting NAG at a rate of 3 g per day in October, 1988. His symptoms improved in three weeks. He continued NAG treatment and reported that at eight months, his symptoms had all been alleviated, including the asthma. He continues to have some sensitivity to caffiene and alcohol, which he avoids, but he can now eat a wide variety of foods including salads and high-fibre items, without difficulty. T.L. no longer suffers nausea and "heaving" each morning as he did previously and feels in good health. He has gained 5 kg and has, since 1988, successfully completed the last two years of a degree at The University of British Columbia.

EXAMPLE 11

Case History—W.R.

W.R., male, age 46, has had Crohn's Disease since the age of 18. W.R. underwent surgery on three occasions with removal of considerable bowel. He suffered subsequently from near-intestinal blockage on several occasions since 1981, and pain and bloating of the intestinal tract almost continuously. He took imodium and prednisone (a corticosteroid). Physicians were reluctant to perform more surgery. W.R. began taking NAG in 1989 and felt that it began to improve his condition in a week or so. He experienced less pain and noted a great increase in his ability to tolerate a wider variety of food which previously would cause severe symptoms. W.R. underwent surgery again in 1989 for residual damage caused by earlier bouts of inflammation. He then resumed ingesting NAG at a rate of 3 to 4 g per day and reports that it is highly effective in controlling his symptoms.

EXAMPLE 12

Case History—S.C.

S.C., female, age 45, had been experiencing food intolerance, including gluten sensitivity. She tried various diets without much success. She began in 1989 to take NAG at 3 g per day. She continued for three months and noticed considerable reduction in food intolerance. Thereafter, she tried other diets without NAG for a year. At that time, she concluded that the NAG treatment was superior to the other dietary measures and resumed NAG treatment late in 1990. S.C. reported that daily NAG treatment enabled her to eat a wider variety of foods without experiencing difficulties as before, and that it has greatly improved her condition.

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

REFERENCES

1. Balazs, E. A., Jeanloz, R. W.: The Amino Sugars. Academic Press, New York, 1965, vol. IIA.
2. Heinegard, D., Paulsson, M.: Extracellular Matrix Biochemistry. Piez, K. A., Reddi, A. H. eds., Elsevier, New York, 1984.

3. Varma, R., Varma, R. S.: Mucopolysaccharides Glycosaminoglycans—of Body Fluids in Health and Disease. W. de Gruyter, New York, 1983.
4. Schachter, H.: Biosynthetic controls that determine the branching and microheterogeneity of protein-bound oligosaccharides. Biochemistry and Cell Biology 1986, 64: 163-181.
5. Lukie, B. E., Forstner, G. G.: Synthesis of intestinal glycoprotein. Incorporation of $^{14}$C-glucosamine in vitro. Biochimica et Biophysica Acta 1972, 261: 353-364.
6. Bert, J. L., Pearce, R. H.: The Interstitium and Microvascular Exchange. Handbook of Physiology—The Cardiovascular System IV, 1984, 521-547.
7. Zubay, G.: Biochemistry 2nd ed. MacMillan Publishing Co., New York, 1988, 663.
8. Burton, A. F., Anderson, F. H.: Decreased incorporation of $^{14}$C-glucosamine relative to [3]H-N-acetyl glucosamine in the intestinal mucosa of patients with inflammatory bowel disease. American Journal of Gastroenterology 1983, 78: 19-22.
9. Burton, A. f., Lockhart, F., Bosnjak, S., Yong, S.: Stimulation by 17-alpha-hydroxyprogesterone of glycoprotein and glycosoaminoglycan synthesis in human placenta in vitro. Biology of the Neonate 1989, 55: 151-155.
10. Fassbender, H. G.: Role of chondrocytes in the development of osteoarthritis. American Journal of Medicine 1987, 83 (supp. 5A) 17-24.
11. Olaison, G., Sjodahl, R., Tagesson, C.: Abnormal Intestinal Permeability in Crohn's Disease. Scandinavian Journal of Gastroenterology, 1990, 25: 321-328.
12. Hollander, D. et al.: Increased intestinal permeability in patients with Crohn's Disease and their relatives. Annals of Internal Medicine 1986, 105: 883-885.
13. Umetsu, T. et al.: Effect of proglumide on glycoprotein synthesis in aspirin-induced gastric erosions in rats. European Journal of Pharmacology 1980, 69: 69-77.

What is claimed is:

1. A method of treating gastrointestinal mucous membrane disorder in the lower gastrointestinal tract of a human being suffering from said gastrointestinal mucous membrane disorder comprising feeding the human being having said gastrointestinal mucous membrane disorder a therapeutically effect amount of N-acetyl glucosamine.

2. A method according to claim 1 wherein the N-acetyl glucosamine is fed to the human being on a daily basis.

3. A method according to claim 2 wherein the human being is fed about 300 mg to about 10,000 mg of N-acetyl glucosamine per day.

4. A method according to claim 2 wherein the human being is fed about 1,000 mg to about 6,000 mg of N-acetyl glucosamine per day.

5. A method according to claim 2 wherein the human being is fed about 500 mg of N-acetyl glucosamine per day.

6. A method according to claim 3 wherein the N-acetyl glucosamine is incorporated in a pharmaceutically acceptable carrier.

* * * * *